(12) United States Patent
Ragauskas et al.

(10) Patent No.: US 8,062,224 B2
(45) Date of Patent: *Nov. 22, 2011

(54) METHOD AND APPARATUS FOR NON-INVASIVE CONTINUOUS MONITORING OF CEREBROVASCULAR AUTOREGULATION STATE

(75) Inventors: Arminas Ragauskas, Kaunas (LT); Gediminas Daubaris, Kaunas (LT)

(73) Assignee: UAB Vittamed, Bethel, CT (US)

( * ) Notice: Subject to any disclaimer, the term of this patent is extended or adjusted under 35 U.S.C. 154(b) by 905 days.

This patent is subject to a terminal disclaimer.

(21) Appl. No.: 11/259,831

(22) Filed: Oct. 27, 2005

(65) Prior Publication Data

US 2006/0094964 A1    May 4, 2006

Related U.S. Application Data

(60) Provisional application No. 60/622,734, filed on Oct. 28, 2004.

(51) Int. Cl.
*A61B 8/08* (2006.01)
(52) U.S. Cl. ...................................... 600/448
(58) Field of Classification Search .................. 600/311, 600/340, 344, 358, 363, 364, 372, 390, 438, 600/454, 459, 465, 480, 484–88, 504, 533, 600/534, 544
See application file for complete search history.

(56) References Cited

U.S. PATENT DOCUMENTS

| | | | |
|---|---|---|---|
| 3,439,530 A | 4/1969 | Flaherty et al. | |
| 3,713,329 A | 1/1973 | Munger | |
| 3,818,989 A | 6/1974 | Christopher, Jr. et al. | |
| 3,872,858 A | 3/1975 | Hudson et al. | |
| 4,043,321 A | 8/1977 | Soldner et al. | |
| 4,062,354 A | 12/1977 | Taylor et al. | |
| 4,312,361 A | 1/1982 | Nicholson et al. | |
| 4,610,255 A | 9/1986 | Shimura et al. | |
| 4,690,149 A | 9/1987 | Ko | |
| 4,819,648 A | 4/1989 | Ko | |
| 4,893,630 A | 1/1990 | Bray, Jr. | |
| 4,960,118 A * | 10/1990 | Pennock | 128/200.24 |
| 4,971,061 A | 11/1990 | Kageyama et al. | |
| 4,984,567 A | 1/1991 | Kageyama et al. | |
| 5,074,310 A | 12/1991 | Mick | |

(Continued)

FOREIGN PATENT DOCUMENTS

JP    2000262480 A    9/2000

(Continued)

OTHER PUBLICATIONS

Berger et al. Respiratory effects on arterial pressure: a novel signal analysis approach. IEEE Engineering in Medicine and Biology Society 10th Annual International Conference. 1988.*

(Continued)

*Primary Examiner* — Parikha Mehta
(74) *Attorney, Agent, or Firm* — St. Onge Steward Johnston & Reens LLC

(57) ABSTRACT

A non-invasive method for continuous real-time monitoring of cerebrovascular blood flow autoregulation state includes simultaneous non-invasive monitoring of intracranial blood volume respiratory waves and lung volume respiratory waves, real-time decomposition of intracranial blood volume respiratory waves and lung volume respiratory waves into narrowband sinewave first harmonic components, determination therefrom of the phase shift between intracranial blood volume respiratory wave and lung volume respiratory wave first harmonics' and derivation of cerebrovascular autoregulation state from that phase shift value.

21 Claims, 14 Drawing Sheets

U.S. PATENT DOCUMENTS

| | | | |
|---|---|---|---|
| 5,117,835 | A | 6/1992 | Mick |
| 5,379,770 | A | 1/1995 | Van Veen |
| 5,388,583 | A | 2/1995 | Ragauskas et al. |
| 5,411,028 | A | 5/1995 | Bonnefous |
| 5,435,312 | A | 7/1995 | Spivey et al. |
| 5,514,146 | A | 5/1996 | Lam et al. |
| 5,617,873 | A | 4/1997 | Yost et al. |
| 5,785,656 | A | 7/1998 | Chiabrera et al. |
| 5,817,018 | A | 10/1998 | Ohtomo |
| 5,840,018 | A | 11/1998 | Michaeli |
| 5,842,990 | A | 12/1998 | Kraske |
| 5,919,144 | A | 7/1999 | Bridger et al. |
| 5,951,476 | A | 9/1999 | Beach |
| 5,951,477 | A | 9/1999 | Ragauskas et al. |
| 5,987,351 | A | 11/1999 | Chance |
| 6,117,089 | A * | 9/2000 | Sinha ............ 600/561 |
| 6,875,176 | B2 | 4/2005 | Mourad et al. |
| 7,198,602 | B2 * | 4/2007 | Eide ............ 600/485 |
| 2002/0095087 | A1 | 7/2002 | Mourad et al. |

FOREIGN PATENT DOCUMENTS

| | | |
|---|---|---|
| JP | 2002017686 A | 1/2002 |
| JP | 2002017687 A | 1/2002 |
| JP | 2002501774 T | 1/2002 |
| WO | 9938433 A1 | 8/1999 |

OTHER PUBLICATIONS

Panerai R B et al. Short-term variability of cerebral blood flow velocity responses to arterial blood pressure transients. *Ultrasound in Med. & Biol.*, vol. 29, No. 1, pp. 31-38, 2003.

Aaslid R et al. Cerebral autoregulation dynamics in humans. *Stroke* 1989;20:45-52.

Czosnyka M et al. Continuous assessment of the cerebral vasomotor reactivity in head injury. *Neurosurgery* 1997;41:11-19.

Panerai R B. Assessment of cerebral pressure autoregulation in humans—a review of measurement methods. *Physiol Meas* 1998;19:305-338.

Panerai R B et al. Linear and nonlinear analysis of human dynamic cerebral autoregulation. *Am J Physiol* 1999a; 277:H1089-H1099.

Zhang R et al. Spontaneous fluctuations in cerebral blood flow: insights from extended-duration recordings in humans. *Am J Physiol Circ Physiol* 278:H1848-H1855,2000; 0363-6135/00 S5.00, vol. 278, Issue 6, H1848-H1855, Jun. 2000.

Schmidt B et al. Adaptive noninvasive assessment of intracranial pressure and cerebral autoregulation. Stroke 2003;43:84-89, 2003.

Strik C et al. Intracranial oscillations of cerebrospinal fluid and blood flow: analysis with magnetic resonance imaging. *Journal of magnetic resonance imaging* 15:251-258, 2002.

Schondorf R et al. Dynamic cerebral autoregulation is preserved in neurally mediated syncope. *J Appl Physiol* 91:2493-2502, 2001.

Parati G et al. Spectral analysis of blood pressure and heart rate variability in evaluating cardiovascular regulation. *Hypertension* 1995;25:1276-1286.

Ragauskas et al. Implementation of non-invasive brain physiological monitoring concepts. *Medical Engineering & Physics* 25(2003) 667-678.

International Search Report & Written Opinion of the International Searching Authority, Apr. 11, 2007, 8 pages.

Lu, et al.; "Cerebral Autoregulation and Gas Exchange Studied Using a Human Cardiopulmonary Model"; Proceedings of the 25th Annual International Conference of the IEEE EMBS; Cancun, Mexico; Sep. 17-21, 2003; 2 pages.

Avezaat, et al.; "Cerebrospinal Fluid Pulse Pressure and Intracranial Volume-Pressure Relationships"; Jouranl of Neurology, Neurosurgery, and Psychiatry; (1979); pp. 687-700.

Extended European Search Report; EP 05 82 4125; Dec. 22, 2009; 7 pages.

Ragauskas, et al.; "Innovative Technologies of head Injury Physiological Monitoring"; ISSN 1392-2114 Ultragarsas, Nr4(37).; (2000); 8 pages.

Czosnyka, et al.; "Monitoring and Interpretation of Intracranial Pressure"; J Neural Neurosurg Psychiatry (2004); pp. 813-821.

Ragauskas, et al.; "Non-Invasive Technologies for Intracranial Pressure/Volume Measurement"; Proceedings—23rd Annual Conference—IEEE/EMBS Oct. 25-28, 2001; 4 pages.

Schmidt, et al.; "Noninvasive Prediction of Intracranial Pressure Curves Using Transcranial Doppler Ultrasonography and Blood Pressure Curves"; Stroke, American Heart Association, Inc.; http://stroke.ahajournals.org/cgi/content/full/28/12/2465; (1997); 16 pages.

Ragauskas, et al.; "Ultrasonic Non-invasive Intracranial Wave Monitor"; Telematics Scientific Lab, Kansas University of Technology, Lithuania; (2002); pp. 34-39.

K. Fountas et al., Is non-invasive monitoring of intracranial pressure waveform analysis possible? Preliminary results of a comparative study of non-invasive vs. invasive intracranial slow-wave waveform analysis monitoring in patients with traumatic brain injury, Med. Sci. Monit. 11(2), CR58-63 (2005).

I. Chambers et al., The clinical application of non-invasive intracranial blood volume pulse wave monitoring, Physiol. Meas. 26 (2005) 1019-1032.

Diniz, P., Adaptive Filtering: Algorithms and Practical Implementation (Third Ed., Springer, 2008).

Winder, S., Analog and Digital Filter Design (Second Ed., Elsevier Science, 2002).

\* cited by examiner

82

| Total | 13 |
|---|---|
| Gender Male Female | 10 (76.9%) 3 (21.1%) |
| Age Mean Range | 31.25 18-64 years |
| Pathology Closed severe traumatic brain injury | 100 % |
| Cerebrovascular autoregulation simultaneous invasive and non-invasive monitoring | 53 one-hour sessions |
| Slow intracranial B waves simultaneous invasive and non-invasive monitoring | 87 one-hour sessions |

84 — Total row
86 — Gender
88 — Age
90 — Pathology

FIG. 2

INTACT CAS

IMPAIRED CAS

METHOD AND APPARATUS FOR NON-INVASIVE CONTINUOUS MONITORING OF CEREBROVASCULAR AUTOREGULATION STATE

PRIOR APPLICATION

Applicants claim priority benefits under 35 U.S.C. §119(e) of U.S. Provisional Patent Application Ser. No. 60/622,734 filed Oct. 28, 2004.

FIELD OF THE INVENTION

The present invention relates to the measurement and monitoring of cerebrovascular autoregulation state.

BACKGROUND OF THE INVENTION

Cerebral blood flow autoregulation has been shown to be affected in a number of important clinical conditions, such as prematurity, birth asphyxia, stroke, head injury, carotid artery disease, hypertension and vasovagal syncope. Acute cerebral diseases (e.g., traumatic brain injury, stroke) frequently lead to a rise in intracranial pressure (ICP) and impairment of cerebral autoregulation (as described in the following references: Aaslid R. et al., Cerebral autoregulation dynamics in humans. *Stroke* 1989; 20:45-52; Czosnyka M. et al., Continuous assessment of the cerebral vasomotor reactivity in head injury. *Neurosurgery* 1997; 41:11-19.; Panerai R. B., Assessment of cerebral pressure autoregulation in humans—a review of measurement methods. *Physiol Meas* 1998; 19:305-338; and Schondorf R. et al., Dynamic cerebral autoregulation is preserved in neurally mediated syncope. *J Appl Physiol* 91:2493-2502, 2001).

Assessment of cerebrovascular autoregulation state (CAS) could be of vital importance in ensuring the efficacy of therapeutic measures in the case of brain injury and stroke. Continuous monitoring of CAS and CAS monitoring data based treatment of intensive care patients with brain injuries or stroke will reduce mortality and morbidity of such patients.

Various methods have previously been introduced to assess CAS. Discrete clinical tests (as described in the following references: Aaslid R. et al., Cerebral autoregulation dynamics in humans. *Stroke* 1989; 20:45-52; and Panerai R. B., Assessment of cerebral pressure autoregulation in humans—a review of measurement methods. *Physiol Meas* 1998; 19:305-338), like e.g. the cuff leg test (as discussed in reference Aaslid R. et al. Cerebral autoregulation dynamics in humans. *Stroke* 1989; 20:45-52) did not provide continuous monitoring data about CAS. There is a need for continuous real-time CAS monitoring because is it the optimal monitoring for use with CAS based therapy.

A few methods and techniques (such as those described in the following references: Czosnyka M et al., Continuous assessment of the cerebral vasomotor reactivity in head injury. *Neurosurgery* 1997; 41:11-19; and Schmidt B et al., Adaptive noninvasive assessment of intracranial pressure and cerebral autoregulation. *Stroke* 2003; 43:84-89, 2003) have been proposed for invasive, semi non-invasive and non-invasive monitoring of CAS. These methods are based on the estimation of the correlation factor between arterial blood pressure (ABP) and ICP slow waves or ABP and cerebral blood flow velocity (CBFV) slow waves (as described in the following references: Czosnyka M et al., Continuous assessment of the cerebral vasomotor reactivity in head injury. *Neurosurgery* 1997; 41:11-19; and Schmidt B et al., Adaptive noninvasive assessment of intracranial pressure and cerebral autoregulation. *Stroke* 2003; 43:84-89, 2003). In the case of intact cerebrovascular autoregulation the correlation factor between ABP and ICP slow waves is negative and close to −1.0. In the case of impaired CAS the same factor is positive and close to +1.0.

The disadvantages of slow invasive or non-invasive ABP and ICP wave correlation monitoring methods, include but are not limited to the following.

First, slow ICP waves are not permanent and the amplitude of such waves is too low (less than 3.0 mmHg during main part of ICU patients' continuous monitoring time) in order to measure such waves with sufficient accuracy. Also, non-invasive measurement or prediction of slow ICP waves adds additional errors and distortions of such waves. Further, if invasive slow ICP wave measurement is replaced by non-invasive transcranial Doppler (TCD) CBFV measurement, additional errors and distortions of such waves will occur. Moreover, slow ABP waves are also too small to measure with sufficient accuracy and non-invasively.

Also, the period of slow ICP or ABP waves is estimated to be from approximately 30 seconds to 120 seconds or more. In order to evaluate the CAS applying the slow wave method, it is necessary to accumulate the measured data during 4.0 minutes or longer. This is a relatively long time period and thus becomes a long term process. Long time period testing of CAS is not always effective because variability of CAS is a short-term process (as described in the following reference: Panerai R B et al., Short-term variability of cerebral blood flow velocity responses to arterial blood pressure transients. *Ultrasound in Med. & Biol.*, Vol. 29, No. 1, pp. 31-38, 2003). Because the time delay of CAS monitoring data, secondary brain insults and injury can take place in ICU coma patients before appearance of the CAS monitoring data. The time delay of the slow wave CAS monitoring method is therefore too long for clinical practice of ICU patients monitoring and CAS based treatment.

Additionally, cerebrovascular autoregulation is complex, nonlinear and a multivariate mechanism with considerable short-term variability (as described in the following reference: Panerai R. B. et al., Short-term variability of cerebral blood flow velocity responses to arterial blood pressure transients. *Ultrasound in Med. & Biol.*, Vol. 29, No. 1, pp. 31-38, 2003). A correlation factor can be applied without problems as an indicator of CAS only in linear autoregulatory systems. However, cerebrovascular autoregulation system is nonlinear (as described in the following reference: Panerai R. B. et al., Linear and nonlinear analysis of human dynamic cerebral autoregulation. *Am J Physiol* 1999a; 277:H1089-H1099). Any correlation factor between a reference signal (ABP slow wave) and a nonlinearly distorted cerebrovascular autoregulation system output signal (ICP or CBFV slow wave) would be a questionable indicator of CAS.

Accordingly, it is an object of the present invention to provide a method and apparatus for continuous real-time CAS monitoring that solves the problems and cures the deficiencies of the prior art methods, apparatuses and techniques.

The present invention provides a method for continuous real-time CAS monitoring which is based on simultaneous, non-invasive monitoring of intracranial blood volume respiratory waves (or other intracraniospinal characteristics related to the respiration processes) and lung volume respiratory waves (or other extracranial physiological characteristics related to the lung respiration processes), real-time decomposition or filtering of intracranial blood volume respiratory waves and lung volume respiratory waves into narrowband sinewave first harmonic components, determination therefrom of the phase shift between intracranial blood volume respiratory wave and lung volume respiratory wave first harmonics' and derivation of cerebrovascular autoregulation state from that phase shift value.

The intracranial blood volume (IBV) and lung volume (LV) respiratory waves have much shorter period (typically 2.5 seconds to 10.0 seconds) than slow waves. Respiratory waves are permanent in all conditions of ICU patients. Lung respiratory waves, as a reference signal for CAS estimation, can be measured non-invasively with accuracy much higher than non-invasive ABP slow wave measurements. Also IBV respiratory waves can be measured non-invasively with much higher accuracy than ICP or IBV slow wave measurements (as described in the following reference: Ragauskas et al., Implementation of non-invasive brain physiological monitoring concepts. *Medical Engineering & Physics* 25(2003) 667-678). It is not necessary to accumulate more than one period of non-invasively recorded IBV and LV respiratory wave data in order to estimate CAS. Because of that, the present invention provides a method of CAS monitoring which is much closer to a real-time method when compared with the slow wave method.

SUMMARY OF THE INVENTION

The present invention is directed to a method and apparatus for non-invasive measuring and for continuous real-time monitoring of cerebrovascular autoregulation state ("CAS"). The method includes simultaneous non-invasive monitoring of intracranial blood volume respiratory waves together with lung volume respiratory waves, also real-time decomposition (or filtering) of intracranial blood volume respiratory waves and lung volume respiratory waves into narrowband sinewave first harmonic components and also determination therefrom of the phase shift between intracranial blood volume respiratory wave and lung volume respiratory wave first harmonics and derivation of the cerebrovascular autoregulation state from that phase shift value. If the phase difference between non-invasively measured intracranial blood volume respiratory waves and lung volume respiratory waves is close to zero that means that cerebrovascular autoregulation is impaired. If the phase difference between intracranial blood volume respiratory waves and lung volume respiratory waves is equal or more than 30 to 40 degrees that means that cerebrovascular autoregulation is intact. Phase difference means severity of impairment of CAS. The smaller the phase difference, the greater the severity of impairment. The threshold value 30 degrees divides the severity into intact CAS and impaired CAS.

The method comprises the steps of generating a first reference signal and a second information signal. The signals are extracted from non-invasively measured or monitored respiratory waves.

The reference signal is non-invasively taken from the place of the human body where the signal consists of essentially changes in lung volume caused by respiration. Typically, this signal can be take from a sensor on the patient's chest but the reference signal can be generated by other means known to those of skill in the art. The reference signal is extracted from lung volume respiratory waves using narrowband adaptive filtering of the first harmonic of the lung volume respiratory wave.

The information signal is non-invasively taken from the intracraniospinal media of the human head or spine. This signal consists of essentially changes of intracranial pressure or intracranial blood volume or other physiological characteristics of intracraniospinal media caused by respiration processes (as described in the following references: Zhang R. et al., Spontaneous fluctuations in cerebral blood flow: insights from extended-duration recordings in humans. *Am J Physiol Circ Physiol* 278:H1848-H1855, 2000; 0363-6135/00 S5.00, Vol. 278, Issue 6, H1848-H1855, June 2000; Strik C. et al., Intracranial oscillations of cerebrospinal fluid and blood flow: analysis with magnetic resonance imaging. *Journal of magnetic resonance imaging* 15:251-258, 2002; Parati G. et al., Spectral analysis of blood pressure and heart rate variability in evaluating cardiovascular regulation. *Hypertension* 1995; 25:1276-1286; and Ragauskas et al., Implementation of non-invasive brain physiological monitoring concepts. *Medical Engineering & Physics* 25(2003) 667-678). The information signal is extracted from intracraniospinal respiratory waves using narrowband adaptive filtering of the first harmonic of the intracraniospinal respiratory wave.

The adaptive narrowband filtering procedures can be identical for both reference and information signals. Because of that, the measurement or monitoring data of the CAS are not affected by the phase shifts of signals in the adaptive narrowband filters of the first harmonics of reference and information signals. Narrowband adaptive filtering of the first harmonics' of reference and information signals eliminates the additional errors of CAS estimation caused by the non-linearity of cerebrovascular blood flow autoregulation system.

In the case of impaired CAS, cerebral vessels responsible for cerebral blood flow autoregulation react passively to ABP or heart rate (HR) changes. In that case, the phase difference between reference and information signals is small and close to zero degrees.

In the case of intact CAS, cerebral vessels responsible for cerebral blood flow autoregulation react actively in order to stabilize the cerebral blood flow within physiological limits of cerebral perfusion pressure (CPP). In that case, the phase difference between reference signal and information signal is typically more than 30 to 40 degrees.

Such phase difference between the first harmonics of the reference signal and the information signal is a reliable estimator of CAS. In order to estimate CAS continuously such phase difference is monitored and displayed continuously in the proposed apparatus of the present invention.

BRIEF DESCRIPTION OF THE DRAWINGS

FIG. 2 is a chart showing a clinical study population.

DETAILED DESCRIPTION OF THE DRAWINGS

Figure 1A:
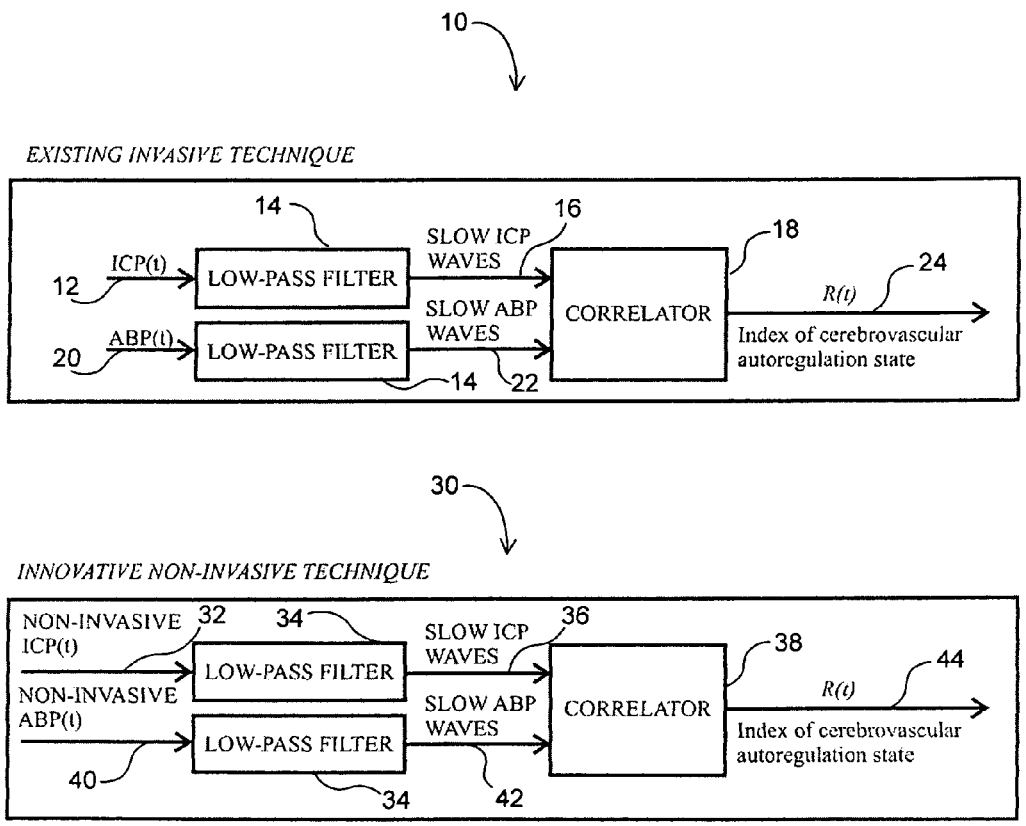
FIG. 1A is a block diagram showing existing prior art invasive techniques and the innovative non-invasive technique.

Thirteen ICU coma patients were studied by simultaneously applying an invasive slow wave CAS monitoring method and non-invasive monitoring method (FIG. 1A). FIG. 1A first shows a block diagram of the present existing invasive monitoring technique 10 (as disclosed in Czosnyka M. et al., Continuous assessment of the cerebral vasomotor reactivity in head injury. *Neurosurgery* 1997; 41:11-19). The invasive monitoring includes invasively measuring the patients ICP, passing the measured data 12 through a low pass filter 14 to generate an output of the slow ICP waves 16 and sending the output to a correlator 18. At the same time, the patient's ABP is monitored invasively and the measured data 20 is passed through a low pass filter 14 to generate an output of the slow ABP waves 22 and sending that output to the correlator 18. The correlator then correlates the two slow wave inputs 16 and 22 to determine an index of cerebrovascular autoregulation state R(t) 24. If the R(t) value is a positive number between 0 and +1.0 then the patient has impaired cerebrovascular autoregulation 26. If the R(t) value is a negative number between 0 and −1.0 then the patient has intact cerebrovascular autoregulation 28.

FIG. 1A also includes a block diagram 30 of an embodiment of the innovative non-invasive technique of the invention. The embodiment includes non-invasively measuring the patients ICP, passing the measured data 32 through a low pass filter 34 to generate an output of the slow ICP waves 36 and sending the output to a correlator 38. At the same time, the patient's ABP is monitored non-invasively and the measured data 40 is passed through a low pass filter 34 to generate an output of the slow ABP waves 42 and sending that output to the correlator 38. The correlator 38 then correlates the two slow wave inputs 36 and 42 to determine an index of cerebrovascular autoregulation state R(t) 44. If the R(t) value is a positive number between 0 and +1.0 then the patient has impaired cerebrovascular autoregulation 26. If the R(t) value is a negative number between 0 and −1.0 then the patient has intact cerebrovascular autoregulation 28.

Clinical data was obtained using invasive ICP monitors "Camino" 420 and "Codman" ICP Express. A non-invasive "Vittamed" monitor (as disclosed in U.S. Pat. No. 5,388,583 and incorporated herein by reference) has been used for non-invasive IBV slow wave, respiratory wave and pulse wave monitoring. An "Ohmeda" Finapress monitor has been used for non-invasive ABP slow wave, respiratory wave and pulse wave monitoring (FIG. 1A).

Figure 1B:
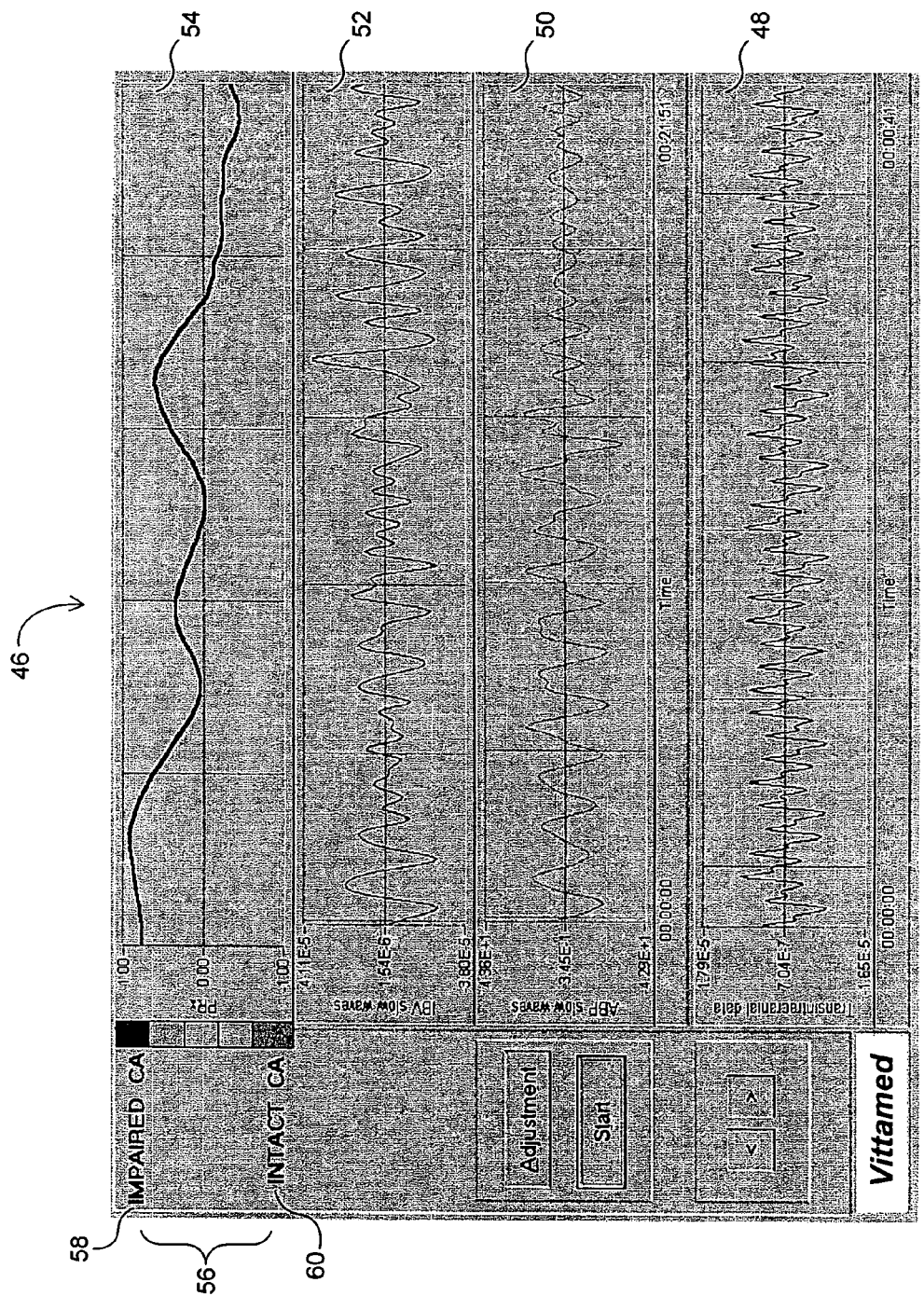
FIG. 1B is a diagram showing an example of IBV and ABP monitored slow waves.

An example of a display of measured waves can be seen in FIG. 1B. FIG. 1B shows an example of displayed waves as are seen on a "Vittamed" monitor 46. The lowest window 48 shows a wave of transintracranial data. The next window up 50 shows a wave of ABP slow wave data. The next window up of the "Vittamed" display 52 (FIG. 1B) shows IBV slow waves monitored non-invasively. Upper window 54 of the display shows CAS estimator PRx—correlation factor R between slow IBV and slow ABP waves. The legend 56 on the upper display window 54 shows that when the PRx value is near +1.0 the CAS is impaired 58 while when the PRx value is near −1.0 the CAS is intact 60.

Figure 1C:
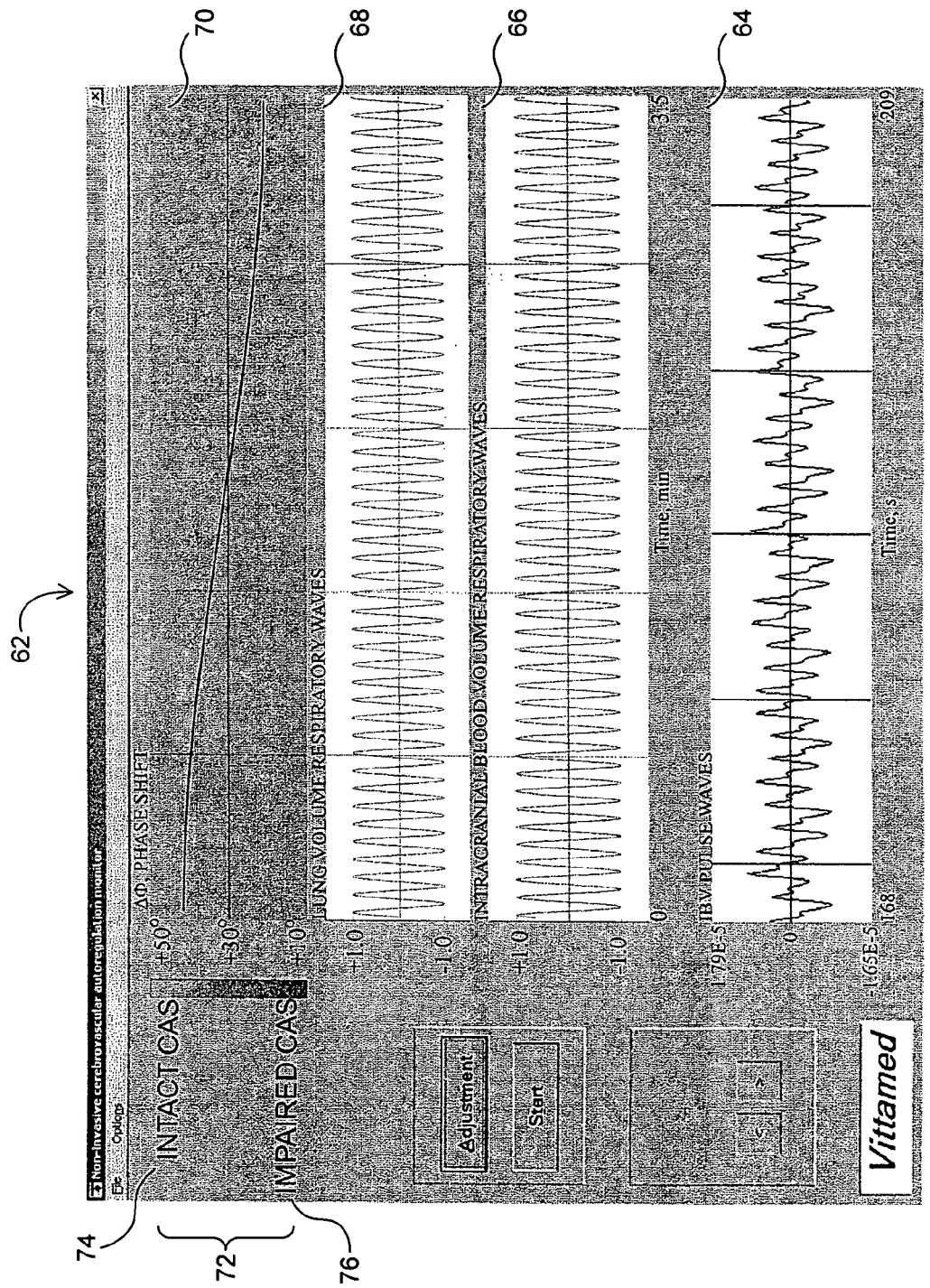
FIG. 1C is a diagram showing an example of IBV and ABP monitored respiratory waves.

Another example of a display of measured waves can be seen in FIG. 1C. The display 62 FIG. 1C shows another example of displayed waves similar to those seen on a "Vittamed" monitor. The lowest window 64 shows IBV pulse waves. The next window 66 up shows intracranial blood volume respiratory waves. The next window 68 up on the display, shows lung volume respiratory waves monitored non-invasively. Upper window 70 of the display shows the phase shift between the filtered intracranial blood volume respiratory waves and the filtered lung volume respiratory waves. The legend 72 on the upper display 70 shows that when the phase shift is above 30 degrees the CAS is intact 74 and when the phase shift is below 30 degrees the CAS is impaired 76.

FIG. 2 is a chart 82 showing a clinical study population. The chart 82 shows the total population of thirteen patients 84 and includes a description of the patients by gender 86, age 88 and pathology 90.

Figure 3:
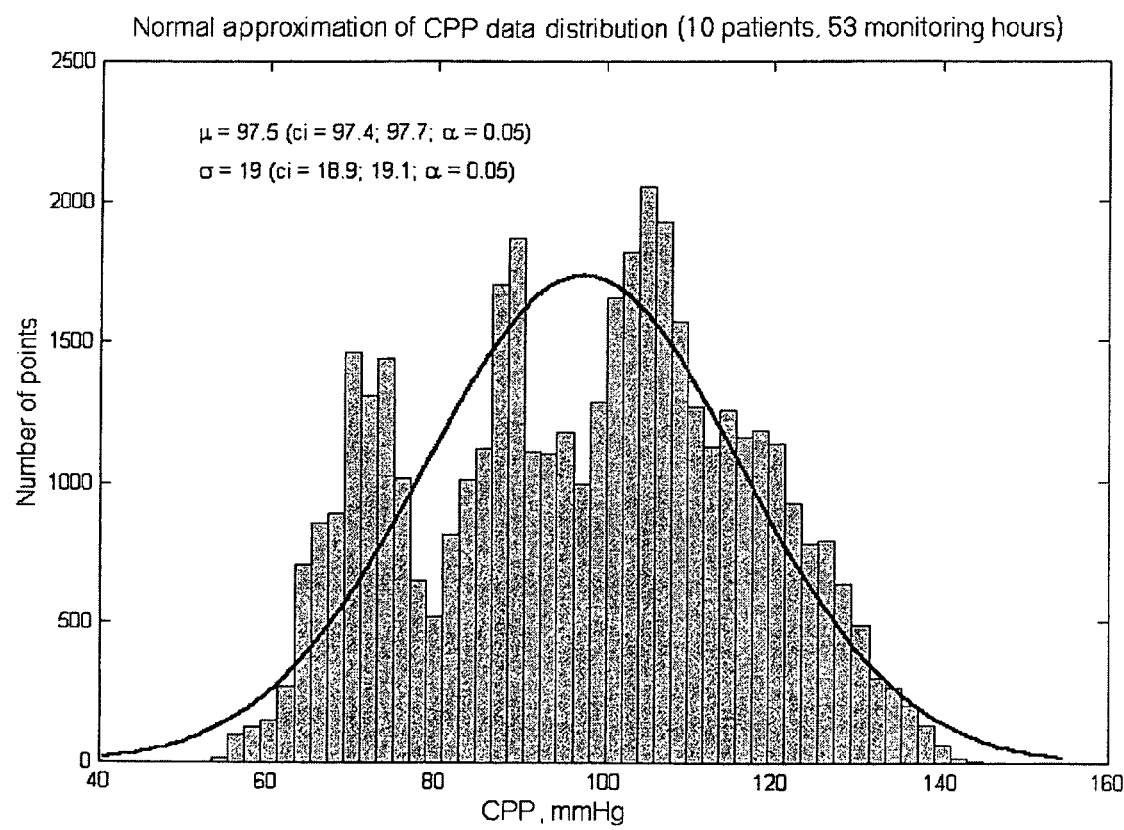
FIG. 3 is a chart showing statistical distribution of CPP data.

The statistical distribution of CPP data (10 coma patients, 53 hours of simultaneous invasive and non-invasive CAS monitoring) is shown on FIG. 3. It is shown (FIG. 3) that our clinical study covered all physiological CPP range.

Figure 4:
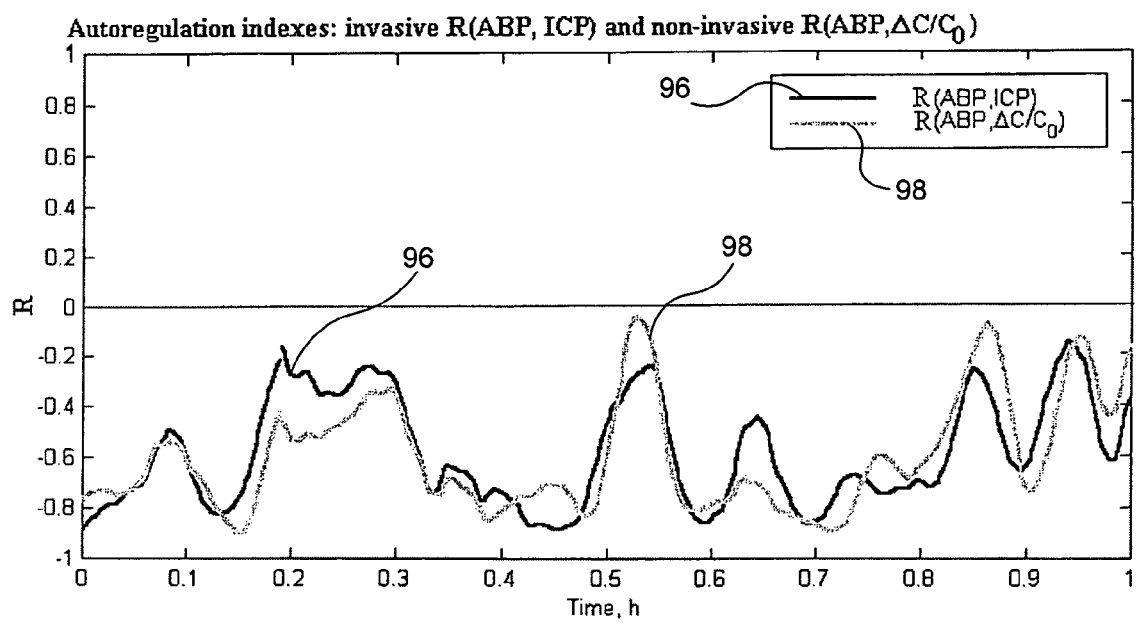
FIG. 4 is a chart showing display results of CAS monitoring.
Figure 5:
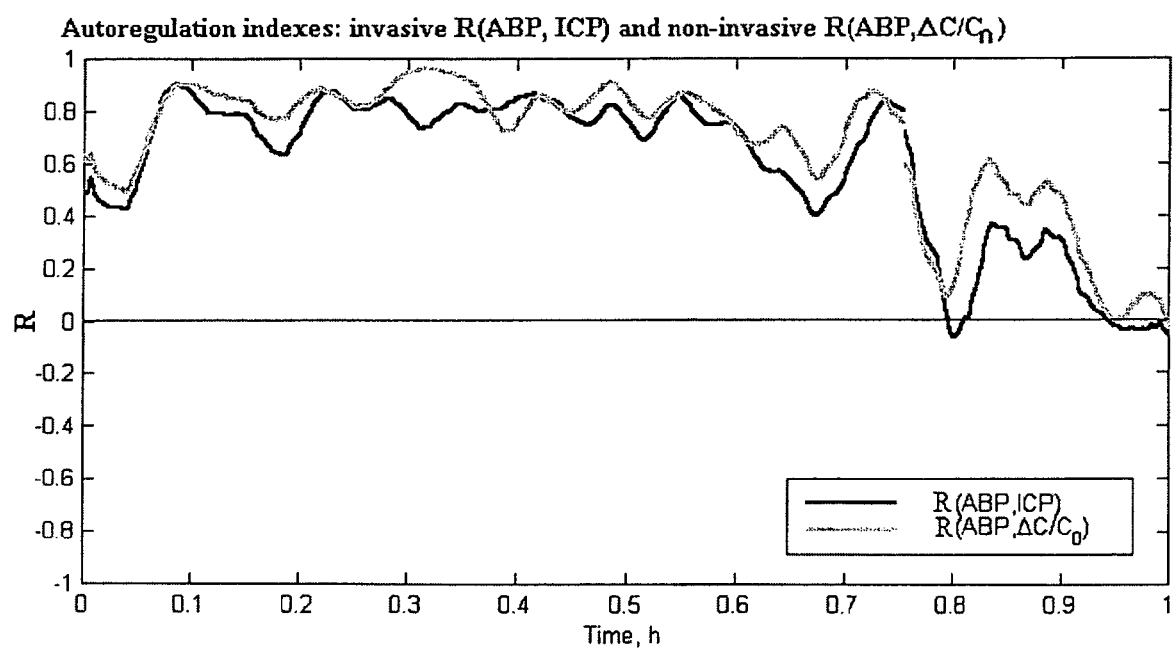
FIG. 5 is a chart showing display results of CAS monitoring.

The results of CAS monitoring are shown in FIG. 4, FIG. 5, FIG. 6 and FIG. 7. FIG. 4 shows the correlation factor between invasively measured ICP and ABP slow waves R (ABP, ICP) 96 and the same factor between simultaneously non-invasively measured IBV and ABP slow waves R(ABP, $\Delta C/C_0$) 98. FIG. 4 shows R values less than zero thus illustrating the case of intact CAS with typical variability. FIG. 5 shows the same correlation factors in the case of impaired CAS. This means the use of non-invasive monitoring gives accurate readings when compared to invasive monitoring.

Figure 6:
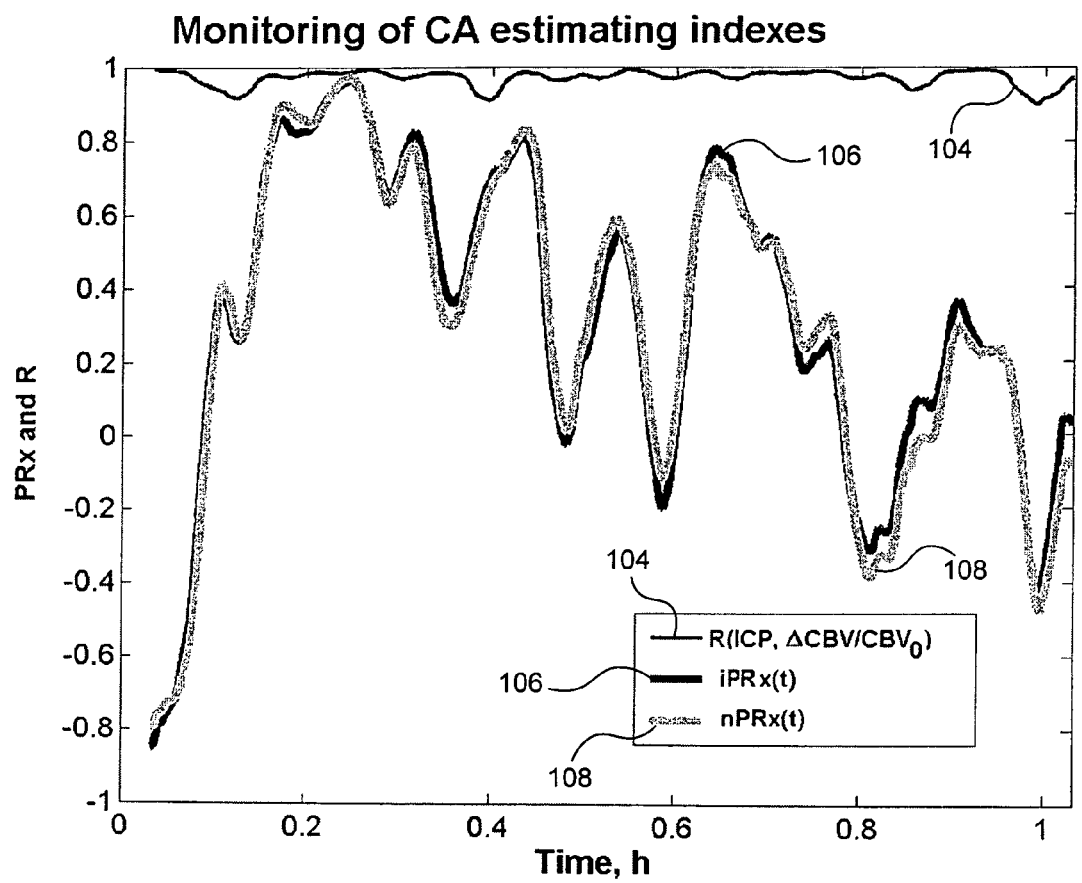
FIG. 6 is a chart showing display results of CAS monitoring.

FIG. 6 shows the same correlation factors in the case of fast change of CAS from intact to impaired. FIG. 6 shows measurements for R (ICP, $\Delta CBV/CBV_0$) 104, iPRx(t) 106 and nPRx(t) 108.

Figure 7:
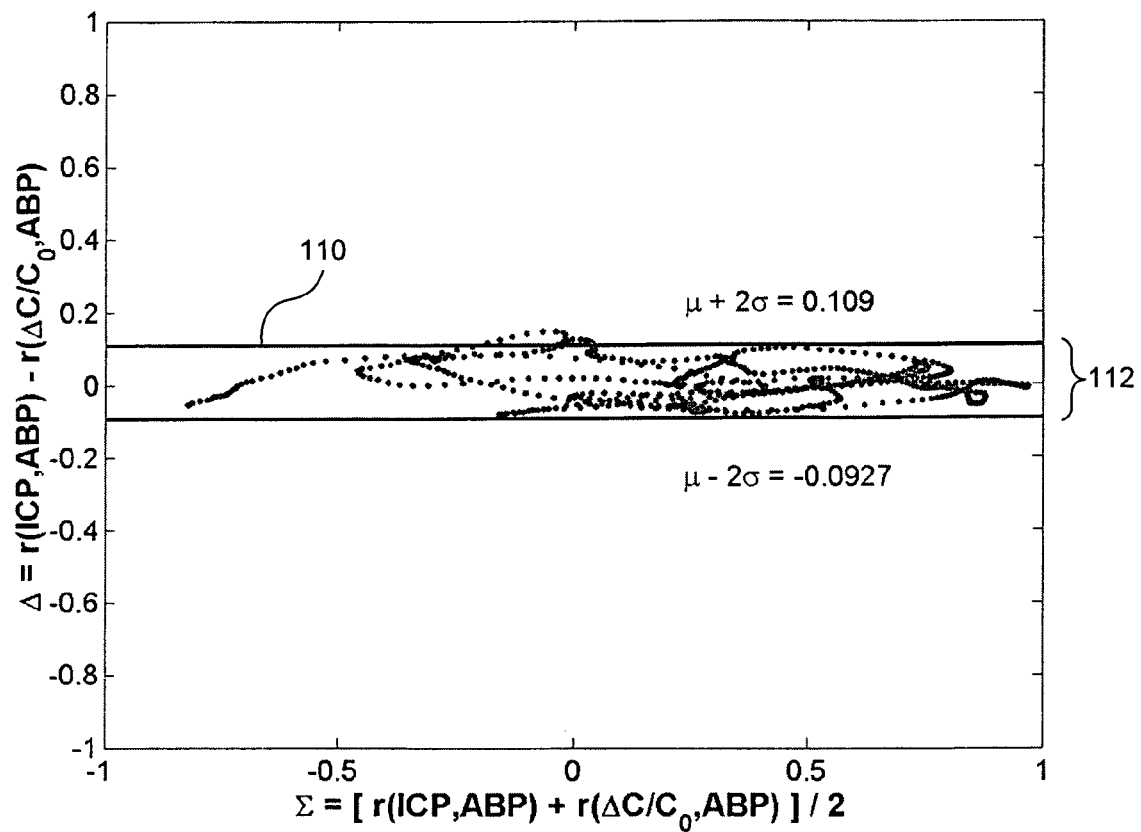
FIG. 7 is a chart showing display results of CAS monitoring.

FIG. 7 shows the Bland Altman plot of the data 110 represented in FIG. 6. It follows from FIG. 7 that invasive and non-invasive CAS monitoring data are in good agreement with uncertainty of such agreement in a range 112 of +/−10%.

Figure 8:
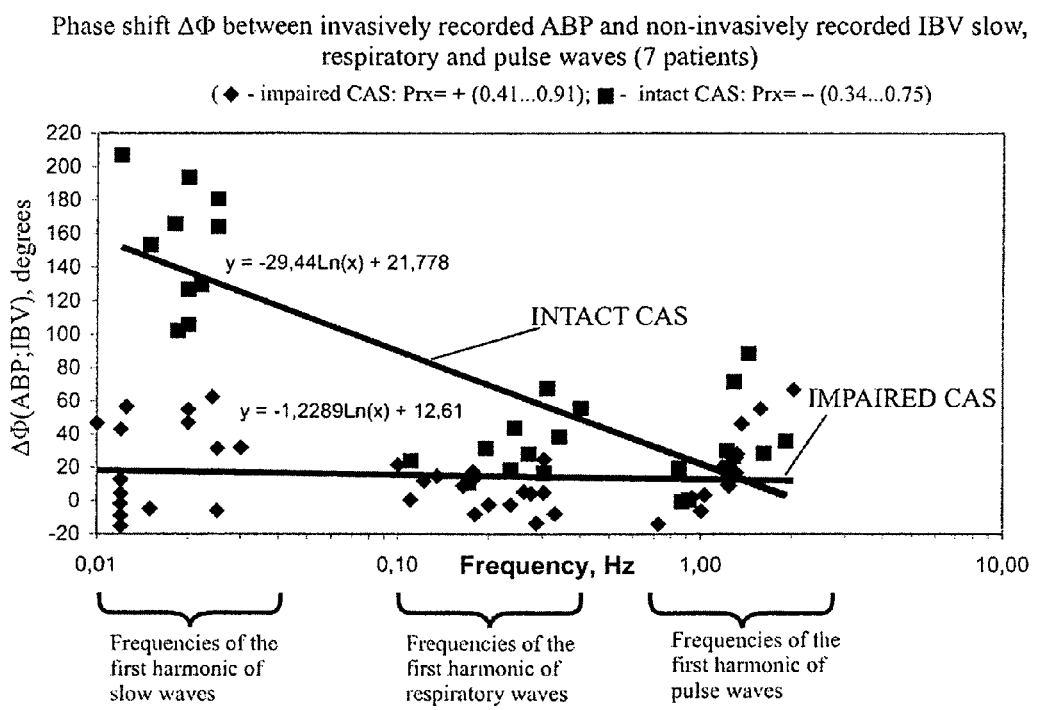
FIG. 8 is a chart showing phase shift measurements resulting from different types of monitoring.

FIG. 8 shows the phase shift between invasively recorded ABP and non-invasively recorded IBV slow, respiratory and pulse waves from 7 patients obtained from the clinical study in the time periods of intact and impaired CAS.

It is seen from FIG. 8 that the phase difference between invasively recorded ABP respiratory waves and IBV respiratory waves is around 60 degrees in the case of intact CAS and it is around 20 degrees in the case of impaired CAS. This result is in good agreement with the same phase differences obtained from the group of healthy subjects (as described in the following reference: Zhang R. et al., Spontaneous fluctuations in cerebral blood flow: insights from extended-duration recordings in humans. *Am J Physiol Circ Physiol* 278: H1848-H1855, 2000; 0363-6135/00 S5.00, Vol. 278, Issue 6, H1848-H1855, June 2000) and also from the group of subjects with neurally mediated syncope (as described in the following reference: Schondorf R. et al., Dynamic cerebral autoregulation is preserved in neurally mediated syncope. *J Appl Physiol* 91:2493-2502, 2001). This result also is evidence that the permanent, continuous respiratory waves can be used as a reference and information signal in CAS assessment and continuous monitoring. Also it is seen from FIG. 8 that the phase difference between the extracranial respiratory wave reference signal and intracranial blood volume respiratory wave information signal reflects the CAS and it is able to distinguish between intact CAS and impaired CAS. Phase difference means severity of impairment of CAS. The smaller the phase difference, the greater the severity of impairment. The threshold value 30 degrees divides the severity into intact CAS and impaired CAS.

FIG. 8 shows some scattering of experimental Δφ points in both cases of intact CAS and impaired CAS. That scattering is caused by the limited signal to noise ratio first of all in the channel of ABP slow wave monitoring. In the present invention this channel is not used because of limited signal to noise ratio and the resulting uncertainty of CAS assessment.

Figure 9:
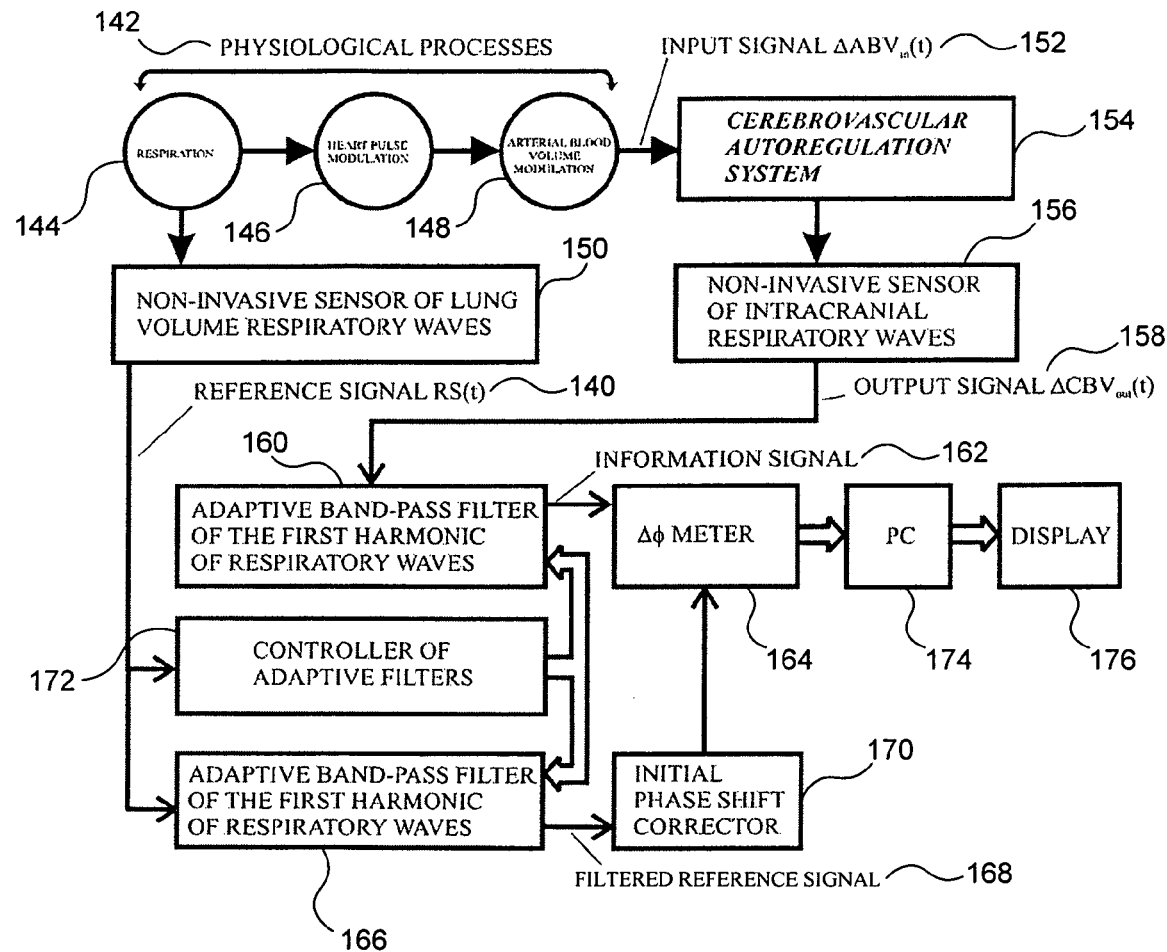
FIG. 9 is a block diagram showing components of a CAS monitoring system.

Non-invasively recorded lung respiration process, an embodiment of which is shown in FIG. 9, is used in this invention as a reference signal RS(t) 140 in order to get much better signal to noise ratio and to reduce the uncertainty of CAS assessment. The block diagram in FIG. 9 shows the physiological processes 142 that are monitored in this embodiment of the invention. The monitored physiological processes include respiration 144, heart pulse modulation 146 and arterial blood volume modulation 148. It is not always necessary for the invention that the heart pulse modulation be measured.

Lung volume changes during the respiratory cycle when respiration occurs with or without mechanical assistance. The changes in lung volume when monitored result in the generation of respiratory waves which can be measured. Under the embodiment of the invention described in FIG. 9 respiration is measured by a non-invasive sensor 150 that measures lung volume respiratory waves. The lung volume changes also modulates ABP 148 and the heart pulse rate (HR) 146. As a result of that, the arterial blood volume in carotid and vertebral arteries (as described in the following reference: Parati G. et al., Spectral analysis of blood pressure and heart rate variability in evaluating cardiovascular regulation. *Hypertension* 1995; 25:1276-1286) reflects the shape and phase of the lung volume respiratory wave with low distortions. Such arterial blood volume respiratory wave is an input signal $\Delta ABV_{in}(t)$ 152 of the cerebrovascular autoregulation system 154. In this embodiment of the invention, the cerebrovascular autoregulation system 154 is monitored by a non-invasive sensor of intracranial respiratory waves 156. The sensor 156, which can be any type of non-invasive sensor known to those of skill in the art, generates an output signal $\Delta CBV_{out}(t)$ 158 that is sent to an adaptive band-pass filter of the first harmonic of respiratory waves 160. The filter 160 generates an information signal 162 that is sent to a Δφ meter 164 that determines the difference in phase between the information signal 162 and the reference signal 140 after it has passed through its own adaptive band-pass filter 166. After the passing through the filter 166 the filtered reference signal 168 is sent to the Δφ meter 164. In the embodiment shown the filtered reference signal 168 is first sent through an initial phase shift corrector 170 before being send to the Δφ meter 164.

The phase of this signal is represented by non-invasively recorded lung volume respiratory wave signal (FIG. 9) which is used as a reference signal RS(t) 140 in this invention.

Non-invasive sensor 150 of lung volume respiratory waves can be based on different state of the art principles. It can be based on the belt type breast movement sensor (e.g., MLT1132 Respiratory Belt Transducer, PowerLab ADInstruments) as shown in the FIG. 12 or the sensors of respiratory gas pressure, volume, humidity, temperature, velocity or flow rate of breathing or others. The main requirement of the lung volume respiratory wave sensor 150 is the accuracy of reflection of aspiration/expiration wave phase. A cost effective non-invasive respiratory belt transducer gives up to 3 times less uncertainty of Δφ measurement compared with invasive or non-invasive ABP sensors because of much better signal to noise ratio.

Non-invasive sensor 156 of intracranial respiratory waves is used in this embodiment of the invention in order to obtain the information signal 162. This sensor 156 can be based on the state of the art non-invasive ultrasonic ICP or IBV respiratory wave sensors (similar to the sensors disclosed in U.S. Pat. Nos. 5,388,583 and 6,387,051 which are incorporated herein by reference) or other ultrasonic, infrared or microwave techniques for non-invasive intracranial respiratory wave monitoring.

The proposed method of CAS monitoring by continuous Δφ measurement (FIG. 9) can be realized also by applying state of the art invasive ICP and ABP respiratory wave sensors.

In order to eliminate the uncertainty of CAS estimation caused by nonlinearity of the cerebrovascular autoregulation system, identical adaptive filters of the first harmonics of respiratory waves 160, 166 can be used in the channels of the information signal 162 and the reference signal 140. Narrow-band adaptive filters can also be controlled by a controller of adaptive filters 172 which performs the adjustments procedure of digital adaptive filters to the first harmonic frequency ω1 of respiratory wave as shown in FIG. 12.

FIG. 9 also shows a PC (personal computer) 174 connected to the Δφ meter 164 for processing the output from the Δφ meter 164. Any type of suitable processor or software can be used to process the signal from the Δφ meter 164. In this embodiment the PC 174 is used to process the signal it receives from the Δφ meter 164 and to send an output to a display 176 to display the Δφ so it can be interpreted by the user of the apparatus. The PC 174 can be used to generate any type of display that users of the system believe would be helpful when monitoring the CAS status. Those of skill in the art would be able to program the PC or create software to generate any variety of appropriate and useful displays.

Figure 10:
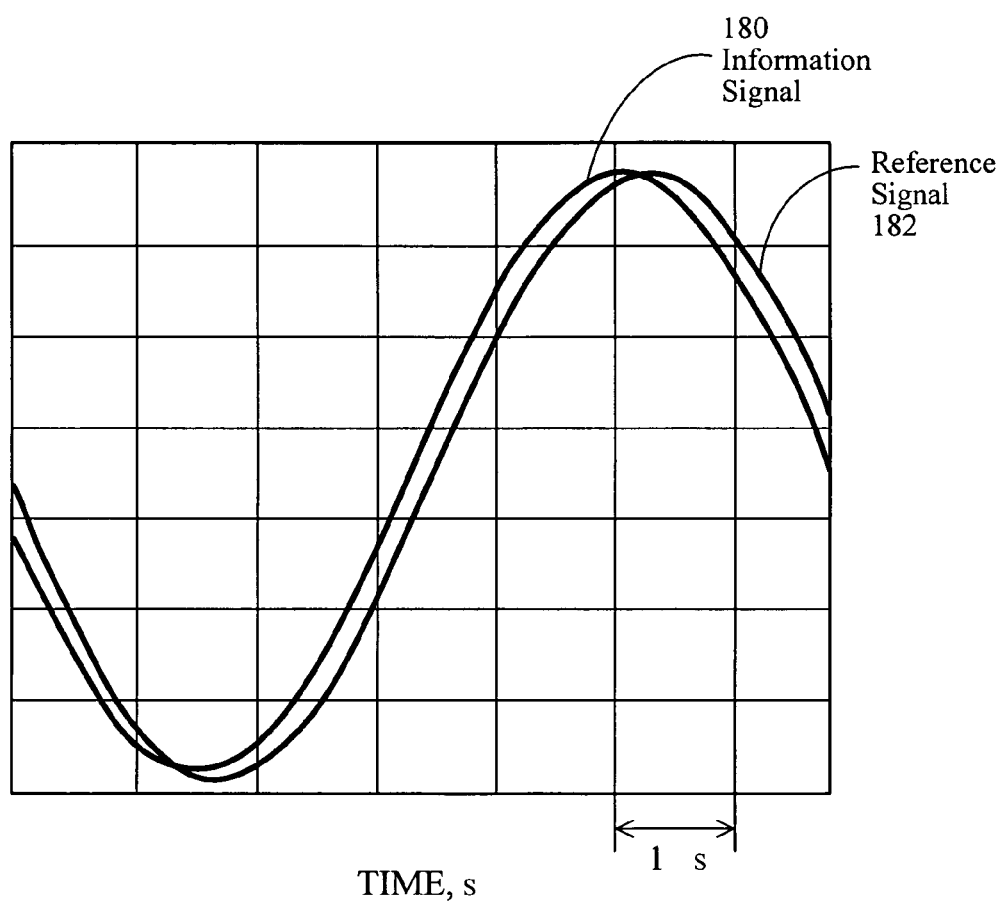
FIG. 10 is a chart showing an information and reference signal when CAS is impaired.
Figure 11:
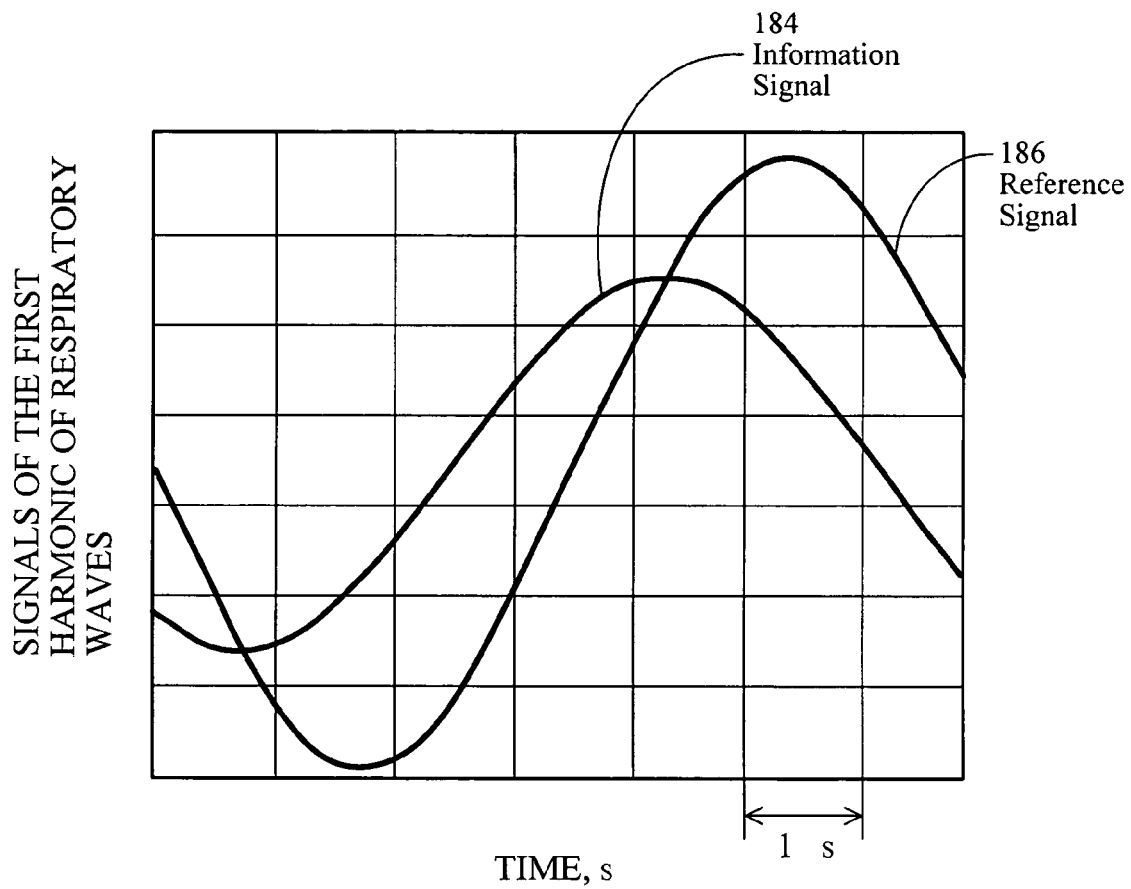
FIG. 11 is a chart showing an information and reference signal when CAS is intact.

FIG. 10 shows an example of a first harmonic of a respiratory wave used as an information signal 180 and of a reference signal 182 in the case of impaired CAS. In FIG. 10 it can be seen that there is very little difference in the phase of the wave signals. In contrast FIG. 11 shows an example of a first harmonic of a respiratory wave used as an information signal 184 and of a reference signal 186 in the case of intact CAS. In FIG. 11, it can be seen that there is a more substantial difference in the phase of the wave signals when the CAS is intact as compared to when the CAS is impaired.

Figure 12:
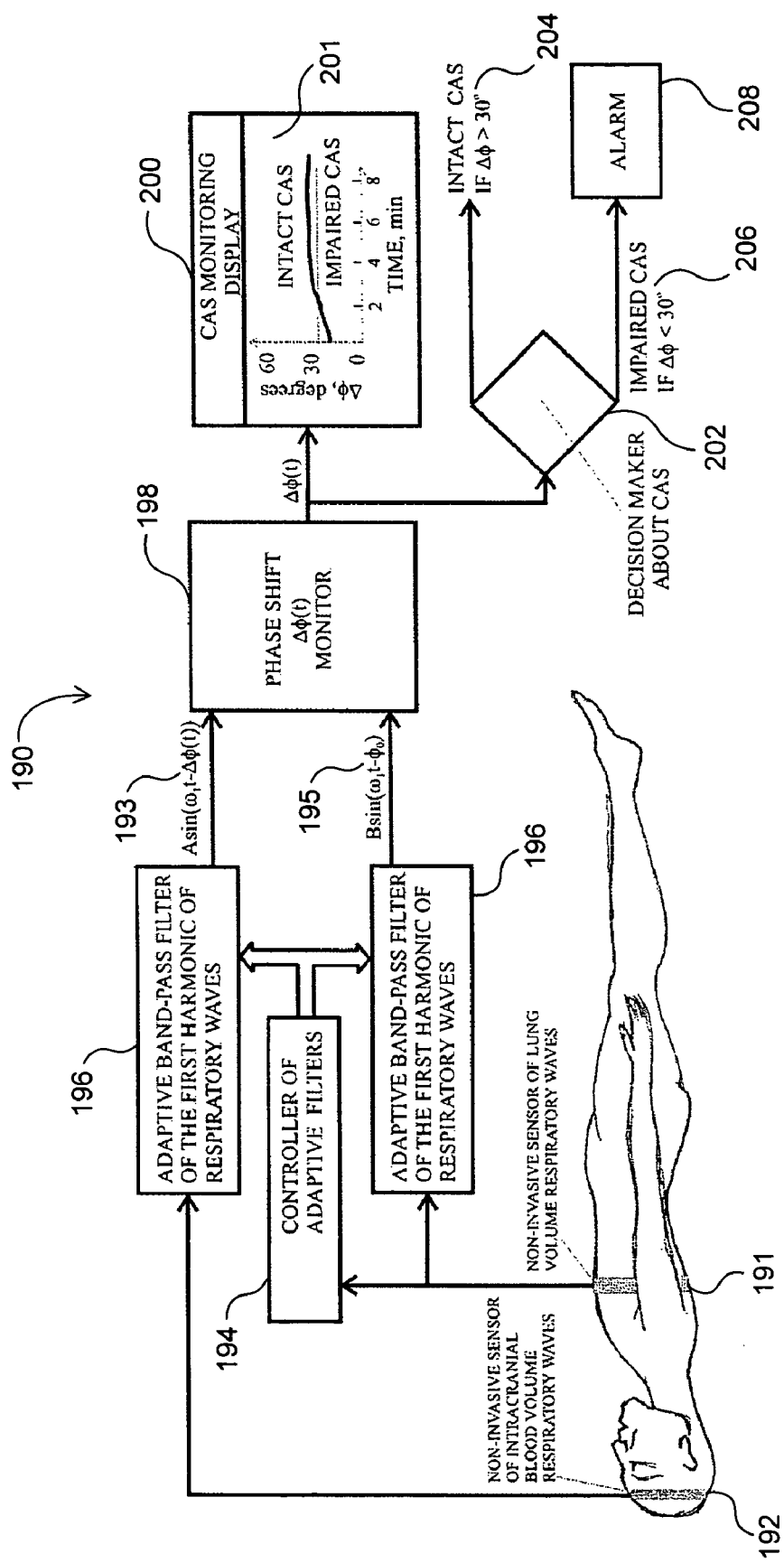
FIG. 12 is a block diagram of an embodiment of the apparatus of the present invention.

Another embodiment of the apparatus 190 of the present invention is shown in the block diagram FIG. 12. The apparatus 190 includes a non-invasive lung volume respiratory wave sensor 191 that is a belt type sensor. The sensor 191 measures lung volume respiratory waves. The apparatus 190 also includes a non-invasive intracranial respiratory wave sensor 192 that is based on ultrasonic time of flight method (as described in the following references Ragauskas et al., Implementation of non-invasive brain physiological monitoring concepts. *Medical Engineering & Physics* 25(2003) 667-678; and in U.S. Pat. Nos. 5,388,583 and 6,387,051 that are incorporated herein by reference). Other types of sensors can also be used. A controller 194, adaptive band-pass filter 196 or other types of filters (including but not limited to digital filters) and a phase difference monitor 198 are connected together as a shown in the block diagram. The adaptive pass band filter 196 that filters the intracranial blood volume respiratory waves generates a filtered output according to the formula $A \sin(\omega_1 t - \Delta\phi(t))$ 193 while the adaptive pass band filter that filters the lung volume respiratory waves generates a filtered output according to the formula $B \sin(\omega_1 t - \phi_0)$ 195. The filtered outputs 193, 195 are then received as an input by the phase shift monitor 198. The controller 194, filters 196 and phase shift monitor 198 are based on state of the art electronic hardware and software known to those of skill in the art. Those of skill in the art will recognize that various types of controllers, filters and phase shift monitors can be substituted in this embodiment.

A CAS monitoring display 200 is connected to the phase shift monitor 198 to graphically display the phase shift so the CAS state, whether intact or impaired, can be determined. Any type computer, TV or other type of visual monitor could be used. In this embodiment the CAS monitoring display 200 shows a graph of the $\Delta\phi$ in degrees on the y-axis verses time on the x-axis. A threshold value of $\Delta\phi$ equal to 30 degrees is also show. If the measured $\Delta\phi$ is greater than the threshold value then the CAS is intact, while if the measured $\Delta\phi$ is less than the threshold value then the CAS is impaired.

This embodiment also has a processor 202 or some other type of decision maker about CAS. The decision maker 202 and monitor 200 can use any state of the art PC, processor or any other type of software solution. The decision maker 202 can be a processor, software or any combination of the two for making a decision about the CAS state. In the embodiment shown the decision maker is given a threshold value of 30 degrees with which to compare the difference in the measured phase shift or $\Delta\phi$. If the $\Delta\phi$ is greater than 30 degrees then the CAS is intact 204. However, if the $\Delta\phi$ is less than 30 degrees then CAS is impaired 206. The embodiment also shows an alarm 208 connected to the decision maker 202. If the decision maker 202 determines CAS is impaired, the decision maker can be programmed to activate the alarm 208 to notify care givers that the patient's CAS is impaired and necessary or corrective actions can or should be taken. The alarm 208 can be any type of visual or audible alarm known to those of skill in the art. The alarm 208 could also be a combination of visual and audible alarms. The decision maker can be controlled by a PC, a smaller processor, software or the like.

The new features of the present invention include application of the lung volume respiratory wave as a permanent, continuous and short time frame reference signal suitable for almost real-time measurements. In the case of mechanically ventilated patients this signal is stable and ideal for CAS monitoring in an ICU. In the case of self respiration, the signal is not stable but that is not a problem because the proposed possibility to select the first harmonic of such signal applying narrowband adaptive first harmonic filter makes the signal more usable.

Also new is the application of non-invasively recorded intracranial blood volume or intracranial pressure respiratory waves as an information signal.

Another feature of the invention is the application of two identical adaptive first harmonic filters controlled by the same controller connected to non-invasive lung respiratory wave sensor. Such solution eliminates the additional phase shifts in the adaptive filters resulting from CAS estimation.

A further feature is the application of belt type non-invasive lung respiratory wave transducer in order to obtain the best possible accuracy of the sinewave form reference signal.

Yet another feature is the application of the phase difference between non-invasively recorded information signals and reference signals in order to estimate CAS.

Also new is the decision making about intact CAS when such phase difference is more than 30 degrees and decision making about the impaired CAS when such phase difference is less than 30 degrees.

What is claimed is:

1. A method for continuous real-time cerebrovascular autoregulation state monitoring comprising the steps of:
    monitoring intracranial blood volume respiratory waves with an intracranial blood volume respiratory wave monitor;
    simultaneously monitoring lung volume respiratory waves with a lung volume respiratory wave monitor;
    generating an information signal from said intracranial blood volume respiratory waves;
    generating a reference signal from said lung volume respiratory waves;
    filtering said information signal into a first wave component;
    filtering said reference signal into a second wave component;
    determining a phase shift between said first signal wave component and said second wave component;
    assigning a value to said phase shift; and
    comparing the assigned phase shift value to a predetermined phase shift threshold value in a processor to determine the cerebrovascular autoregulation state.

2. The method of claim 1 wherein said first wave component and said second wave component are both first harmonic wave components.

3. The method of claim 1 wherein said phase shift threshold value is approximately 30 to 40 degrees.

4. The method of claim 3 including the step of determining said cerebrovascular autoregulation state is intact when said assigned phase shift value is equal or more than the threshold value.

5. The method of claim 3 including the step of determining said cerebrovascular autoregulation state is impaired when said assigned phase shift value is less than the threshold value.

6. The method of claim 1 further including displaying the cerebrovascular autoregulation state on a monitor.

7. The method of claim 5 further including activating an alarm when said cerebrovascular autoregulation state is determined to be impaired.

8. A method for continuous real-time cerebrovascular autoregulation state monitoring comprising the steps of:
    non-invasively monitoring intracranial blood volume respiratory waves to create an information signal;
    simultaneously non-invasively monitoring lung volume respiratory waves to create a reference signal;
    filtering said intracranial blood volume respiratory waves and said lung volume respiratory waves into narrowband sine-wave first harmonic components;
    determining the phase shift between the filtered intracranial blood volume respiratory wave and the filtered lung volume respiratory wave;
    assigning a value to said phase shift;
    predetermining a phase shift threshold value and storing said threshold value in a processor;
    comparing the assigned phase shift value to the predetermined phase shift threshold value in a processor; and
    activating an alarm when the assigned phase shift value is less than the phase shift threshold value.

9. An apparatus for continuous real-time cerebrovascular autoregulation state monitoring comprising:
    a first sensor configured to measure intracranial blood volume respiratory waves and generating a blood volume output measurement in the form of a wave;
    a second sensor configured to measure lung volume respiratory waves and generating a lung volume output measurement in the form of a wave;
    a first filter connected to said first sensor configured to receive the blood volume output wave measurement from the first sensor, filtering the blood volume output wave measurement and generating a first filter output;
    a second filter connected to said second sensor configured to receive the lung volume output wave measurement from the second sensor, filtering the lung volume output wave measurement and generating a second filter output;

a phase shift monitor connected to both the first filter and the second filter that receives the first filter output and second filter output and that compares the first filter output to the second filter output to determine the phase shift between the first filter output and second filter output, said phase shift monitor then generates a phase shift value output;

a processor configured to receive the phase shift value output from the phase shift monitor, said processor also having a stored predetermined threshold value, and configured to compare said phase shift value output with said threshold value to determine the status of the cerebrovascular autoregulation state; and a display connected to said processor, said display configured to display information related to the status of the cerebrovascular autoregulation state.

10. The apparatus of claim 9 wherein said first sensor is a non-invasive sensor.

11. The apparatus of claim 9 wherein said second sensor is a non-invasive sensor.

12. The apparatus of claim 11 wherein said second sensor is a belt type lung respiratory wave transducer.

13. The apparatus of claim 9 wherein said first filter generates an output indicative of a component of the blood volume respiratory wave and said second filter generates an output indicative of a component of the lung volume respiratory wave.

14. The apparatus of claim 13 wherein said component of the blood volume respiratory wave and said component of the lung volume respiratory wave are each a sine wave first harmonic component.

15. The apparatus of claim 14 wherein the sine wave first harmonic component of the blood volume respiratory wave is derived from the formula $A \sin(\omega_1 t - \Delta\phi(t))$.

16. The apparatus of claim 14 wherein the sine wave first harmonic component of the lung volume respiratory wave is derived from the formula $B \sin(\omega_1 t - \phi_0(t))$.

17. The apparatus of claim 9 wherein said first filter and second filter are both adaptive band-pass filters.

18. The apparatus of claim 17 wherein said adaptive band-pass filters are filters of the first harmonic of the intracranial blood volume respiratory waves.

19. The apparatus of claim 9 wherein said first filter and second filter are connected to and controlled by a controller of adaptive filters.

20. The apparatus of claim 9 including a monitor connected to said phase shift monitor configured to visually display the phase shift value determined by the phase shift monitor.

21. The apparatus of claim 9 including an alarm connected to said processor configured to receive a signal from said processor to activate said alarm if the processor determines the phase shift value falls below the threshold value indicating an impaired cerebrovascular autoregulation state.

* * * * *